(12) United States Patent
Daum et al.

(10) Patent No.: US 6,800,721 B1
(45) Date of Patent: Oct. 5, 2004

(54) UNSATURATED OLIGOPHENOL CYANATES

(75) Inventors: Ulrich Daum, Hofstetten (CH);
Alessandro Falchetto, Domodossola (IT)

(73) Assignee: Lonza AG, Basel (CH)

( * ) Notice: Subject to any disclaimer, the term of this patent is extended or adjusted under 35 U.S.C. 154(b) by 0 days.

(21) Appl. No.: 09/762,579

(22) PCT Filed: Aug. 9, 1999

(86) PCT No.: PCT/EP99/05757

§ 371 (c)(1),
(2), (4) Date: Feb. 9, 2001

(87) PCT Pub. No.: WO00/09477

PCT Pub. Date: Feb. 24, 2000

Related U.S. Application Data

(60) Provisional application No. 60/096,253, filed on Aug. 12, 1998.

(30) Foreign Application Priority Data

Aug. 11, 1998 (EP) .............................................. 98202692

(51) Int. Cl.[7] ...................... C08G 73/00; C07D 251/32; C07C 261/00
(52) U.S. Cl. ........................ 528/422; 544/193; 560/301
(58) Field of Search ......................... 560/301; 528/422; 544/193

(56) References Cited

U.S. PATENT DOCUMENTS

| | | | |
|---|---|---|---|
| 4,713,442 A | 12/1987 | Woo et al. | 528/422 |
| 4,751,323 A | 6/1988 | Woo et al. | 560/301 |
| 5,932,762 A * | 8/1999 | Falchetto et al. | 560/301 |

FOREIGN PATENT DOCUMENTS

| | | |
|---|---|---|
| EP | 0147548 | 7/1985 |
| EP | 0315089 | 5/1989 |

\* cited by examiner

*Primary Examiner*—Ba K. Trinh
*Assistant Examiner*—Taylor Victor Oh
(74) *Attorney, Agent, or Firm*—Fisher, Christen & Sabol

(57) ABSTRACT

The unsaturated oligophenol cyanates of the general formula $$[A—]_n[B—A—]_xB[—A]_m \quad (I)$$

in which A is a group of formula:

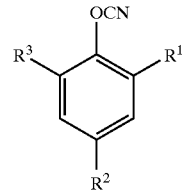

and B is a group of formula:

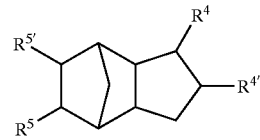

where $R^1$, $R^2$ and $R^3$ are each hydrogen or a bond with a group B, there being either one or two bonds with group B; and both $R^4$ and $R^{4'}$ as well as $R^5$ and $R^{5'}$ separately or jointly represent a direct bond or hydrogen and a bond with a group A, there being either one or two bonds with A. The indices m and n are 0 or 1 but not both 1 at the same time and x is a whole number between 0 and 10, where at least one of the numbers, m, n and x is not 0. The unsaturated oligophenol cyanates can be prepared by reacting the corresponding oligophenols with cyanogen chloride. The have a low viscosity and owing to their double bonds are able to undergo free-radical polymerization. They are especially suitable for use as matrix materials for fiber-reinforced composites and for radiation-curable varnishes and coatings.

11 Claims, No Drawings

UNSATURATED OLIGOPHENOL CYANATES

This application is a continuation (national stage) application of International (PCT) Patent Application No. PCT/EP99/05757, filed on Aug. 9, 1999, which is a continuing application of U.S. Provisional Application Ser. No. 60/096,253, filed on Aug. 12, 1998, and both International Patent Application No. PCT/EP99/05757 and U.S. Provisional Application Ser. No. 60/096,253 have benefit of the priority of European Patent Application No. 98202692.4, filed on Aug. 11, 1998.

BACKGROUND OF THE INVENTION

Field of the Invention

The Invention relates to oligophenol cyanates of the general formula

In this formula, A is in each case a group of the formula

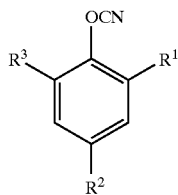

and B is in each case a group of the formula

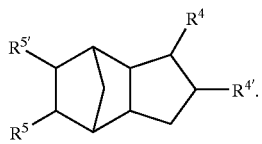

$R^1$, $R^2$ and $R^3$ on each group A independently of the others are in each case hydrogen or a bond to a group B with the proviso that each group A has either one or two bonds to B.

Both $R^4$ and $R^{4'}$, and $R^5$ and $R^{5'}$, on each group B independently of the others, are in each case either together a direct bond or, in any desired order, are hydrogen and a bond to a group A with the proviso that each group B has either one or two bonds to A. The indices m and n are 0 or 1 and x is an integer from 0 to 10 with the proviso that at least one of the numbers m, n and x is other than 0 and m and n are not both at the same time 1.

The Invention also relates in particular to mixtures of such compounds with one another and/or with those compounds of the formula I in which m and n deviate from the above definitions by both, being 1.

BACKGROUND ART

Saturated oligophenol cyanates of general formula I in which m and n deviate from the compounds of the present invention by both being 1 are known, for example, from EP-A-0 147 548 and are marketed by the Dow Chemical Co. under the designation XU71787. These compounds do not have any olefinic double bonds and are therefore able to polymerize only by cyclotrimerization of the cyanate groups or by reaction with functional groups of other compounds. The cyclotrimerization requires the presence of catalysts and/or high temperatures. In contrast it is often desirable to achieve partial curing or crosslinking by means, for example, of irradiation at room temperature. In addition, these known compounds have a relatively high viscosity, which is unfavourable for some applications.

BROAD DESCRIPTION OF THE INVENTION

The object of the present invention was therefore to provide oligophenol cyanates which have a low viscosity and which without further additives can be (partially) polymerized or crosslinked at room temperature by means, for example of radiation-induced free-radical reactions.

In accordance with the invention this object is achieved by the unsaturated oligophenol cyanates of the formula I of the invention. The molecule of these compounds has at least one olefinic double bond ($R^4$—$R^{4'}$ and/or $R^5$—$R^{5'}$ according to the formula I) which permits free-radical addition polymerization.

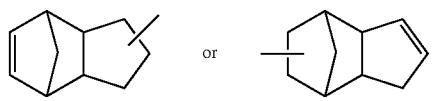

The degree of polymerization, x, lies preferably between 0 and 5 and, with particular preference, between 0 and 3.

The unsaturated oligophenol cyanates of the invention can be prepared by reacting an oligophenol of the general formula:

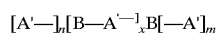      II in which A' is a group of the formula:

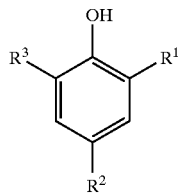

and B, $R^1$, $R^2$, $R^3$, $R^4$, $R^{4'}$, $R^5$, $R^{5'}$, m, n and x are as defined above and elsewhere herein, is reacted with cyanogen chloride in the presence of a tertiary amine. Oligophenols of formula II are obtainable from Borden Chemical Inc. under the designations ESD-X1 to -X5, ESD-472C and ESD-473C. The, compounds concerned here are condensation products of dicyclopentadiene (dimeric cyclopentadiene) and phenol, which are present as a mixture of isomeric and/or homologous compounds and also contain fractions of saturated compounds where m=n=1.

DETAILED DESCRIPTION OF THE INVENTION

The preparation of the oligophenol cyanates of the invention is preferably carried out at a temperature of less than 10° C. in a polar solvent such as butyl acetate and/or acetone or methyl ethyl ketone, for example, or in mixtures of these solvents. Particularly preferred reaction temperatures are below 0° C.—for example, -10° C. It is advantageous to employ 1.0–1.1 mol of tertiary amine and 1.0–1.2 mol of cyanogen chloride per OH equivalent of the oligophenol II. A particularly preferred tertiary amine is triethylamine.

The unsaturated oligophenol cyanates of the invention have a low viscosity at processing temperature and produce polytriazine resins having a particularly low dielectric constant. They are particularly suitable, for example, as matrix material for the production of fibre-reinforced composites, especially for components in aerospace technology, or as base materials for the production of printed circuit boards. Owing to their low viscosity and capacity for polymerization by means of high-energy radiation (UV, X-rays, y-rays or electron beams), they are also suitable for (photo) lithographic varnishes, solder resists for circuit boards, or other radiation-curable lacquers and coatings.

By way of summary, the invention involves an unsaturated oligophenol cyanate of the formula:

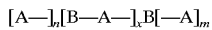  I in which A is in each case a group of formula:

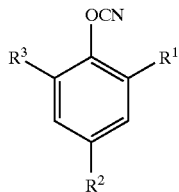  III and B is in each case a group of formula:

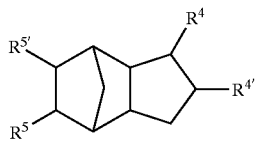  IV wherein $R^1$, $R^2$ and $R^3$ each, independent of one another, are hydrogen or a bond to a group B with the proviso that each group A has either one or two bonds to group B; (i) $R^4$ and $R^{4'}$, and (ii) $R^5$ and $R^{5'}$ each, independent of one another, are either together a direct bond or are hydrogen and a bond to a group A, with the proviso that each group B has either one or two bonds to group A; the indices m and n are 0 or 1 and x is an integer from 0 to 10, with the proviso that at least one of the numbers m, n, and x is other than 0 and m and n are not both at the same time 1; or a mixture of (a) at least two unsaturated oligophenol cyanates of formula I or (b) at least one unsaturated oligophenol cyanate of formula I and at least one unsaturated oligophenol cyanate of formula:

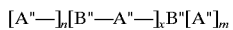  I"

in which A" is in each case a group of formula 11 and B" in each case is a group of formula III, wherein $R^1$, $R^2$ and $R^3$ each, independent of one another, are hydrogen or a bond to a group B" with the proviso that each group A" has either one or two bonds to group B"; (i) $R^4$ and $R^{4'}$, and (ii) $R^5$ and $R^{5'}$ each, independent of one another, are either together a direct bond or are hydrogen and a bond to a group A", with the proviso that each group B" has either one or two bonds to group A"; the indices m and n are each 1 and x is an integer from 0 to 10.

The following example illustrates the preparation of the oligophenol cyanates of the invention without constituting any restriction.

EXAMPLE

Oligophenol ESD-X3 (Borden Chemical Inc.) was dissolved in n-butyl acetate/acetone (v/v=80:20) to give a 15% strength solution. The solution was cooled to −10° C. and, at this temperature, 105% of the calculated amount of triethylamine and then, over the course of 30 minutes, 110% of the calculated amount of cyanogen chloride were added. After a further 30 minutes of reaction, the mixture was subjected to extraction with water, twice at 30° C., in order to remove the ammonium salts formed, and was then passed twice through a falling-film evaporator in order to remove the solvent and the by-product, N,N-diethylcyanamide.

Yield: about 100% properties:

viscosity: 165 mP·s (at 125° C.)

degree of reaction: (phenol→cyanate) >98% gel time: 25 min (at 200° C.)

carbamates: <1%

N,N-diethylcyanamide: <2000 ppm.

What is claimed is:

1. At least one unsaturated oligophenol cyanate selected from the group consisting of:

(I) an unsaturated oligophenol cyanate of the formula:

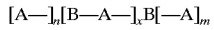  I in which A is in each case a group of formula:

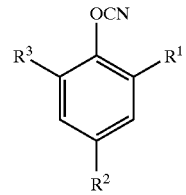  III and B is in each case a group of formula:

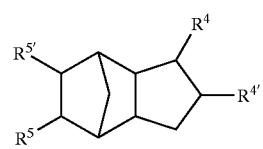  IV wherein $R^1$, $R^2$ and $R^3$ each, independent of one another, are hydrogen or a bond to a group B with the proviso that each group A has either one or two bonds to a group B; (i) $R^4$ and $R^{4'}$, and (ii) $R^5$ and $R^{5'}$ each, independent of one another, are either together a direct bond or are hydrogen and a bond to a group A, with the proviso that at least one of (i) $R^4$ and $R^{4'}$ and (ii) $R^5$ and $R^{5'}$ of at least one group B are together a direct bond, and with the proviso that each group B has either one or two bonds to a group A; the indices m and n independent of one another are 0 or 1 and x is an integer from 0 to 10, with the proviso that at least one of the numbers m, n, and x is other than 0 and m and n are not both at the same time 1;

(II) a mixture of at least two unsaturated oligophenol cyanates of formula I; and (III) a mixture of at least one unsaturated oligophenol cyanate of formula I and at least one compound of formula I in which n and m deviate from the above definitions by both being 1.

2. The at least one unsaturated oligophenol cyanate according to claim 1, wherein x is from 0 to 5.

3. A process for preparing the at least one unsaturated oligophenol cyanate according to claim 1, comprising reacting at least one oligophenol of the formula:

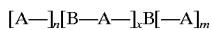

in which A is a group of the formula:

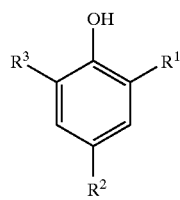

and B, $R^1$, $R^2$, $R^3$, $R^4$, $R^5$, $R^6$, m, n and x are as previously defined with cyanogen chloride in the presence of a tertiary amine.

4. A process comprising preparing a radiation-curable lacquer comprising the at least one unsaturated oligophenol cyanate according to claim 1.

5. The radiation-curable lacquer prepared by the process according to claim 4.

6. A process comprising applying the radiation-curable lacquer according to claim 5 and radiation-curing the radiation-curable lacquer.

7. A process comprising preparing a radiation-curable varnish comprising the at least one unsaturated oligophenol cyanate according to claim 1.

8. The process according to claim 7, wherein the radiation-curable varnish is a radiation curable lithographic varnish.

9. The radiation-curable varnish prepared by the process according to claim 7.

10. The radiation-curable lithographic varnish prepared by the process according to claim 8.

11. At least one unsaturated oligophenol cyanate selected from the group consisting of:

(I) an unsaturated oligophenol cyanate of the formula:

in which A is in each case a group of formula:

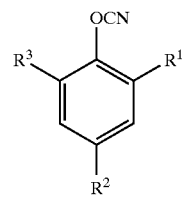

and B is in each case a group of formula:

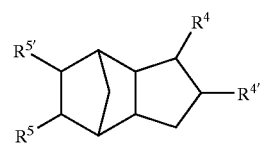

wherein $R^1$, $R^2$ and $R^3$ each, independent of one another, are hydrogen or a bond to a group B with the proviso that each group A has either one or two bonds to a group B; (i) $R^4$ and $R^{4'}$, and (ii) $R^5$ and $R^{5'}$ each, independent of one another, are either together a direct bond or are hydrogen and a bond to a group A, with the proviso that at least one of (i) $R^4$ and $R^{4'}$ and (ii) $R^5$ and $R^{5'}$ of at least one group B are together a direct bond, and with the proviso that each group B has either one or two bonds to a group A; the indices m and n independent of one another are 0 or 1 and x is an integer from 0 to 10, with the proviso that at least one of the numbers m, n, and x is other than 0 and m and n are not both at the same time 1; (II) a mixture of at least two unsaturated oligophenol cyanates of formula I; and (III) a mixture of at least one unsaturated oligophenol cyanate of formula I and at least one unsaturated oligophenol cyanate of formula:

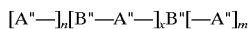

in which A" is in each case a group of formula II and B" in each case is a group of formula III, wherein $R^1$, $R^2$ and $R^3$ each, independent of one another, are hydrogen or a bond to a group B" with the proviso that each group A" has either one or two bonds to group B"; (i) $R^4$ and $R^{4'}$, and (ii) $R^5$ and $R^{5'}$ each, independent of another, are either together a direct bond or are hydrogen and a bond to a ground A", with the proviso that each group B" has either one or two bonds to group A"; the indices m and n are each 1 and x is an integer from 0 to 10.

* * * * *